United States Patent [19]
Jiang et al.

[11] Patent Number: 5,814,128
[45] Date of Patent: *Sep. 29, 1998

[54] WATER MANAGEMENT DEVICE FOR GAS CHROMATOGRAPHY SAMPLE CONCENTRATION

[75] Inventors: Kenneth K. Jiang; Bernie B. Bernard, both of College Station, Tex.

[73] Assignee: OI Corporation, College Station, Tex.

[ * ] Notice: The term of this patent shall not extend beyond the expiration date of Pat. No. 5,358,557.

[21] Appl. No.: 762,666

[22] Filed: Dec. 9, 1996

Related U.S. Application Data

[63] Continuation of Ser. No. 562,840, Nov. 27, 1995, Pat. No. 5,582,633, which is a continuation of Ser. No. 282,171, Jul. 29, 1994, Pat. No. 5,470,380, which is a division of Ser. No. 61,986, May 14, 1993, Pat. No. 5,358,557, which is a division of Ser. No. 848,395, Mar. 9, 1992, Pat. No. 5,250,093.

[51] Int. Cl.$^6$ ................................................. B01D 15/08
[52] U.S. Cl. .................................. 95/82; 95/220; 95/228; 95/261
[58] Field of Search ................................. 95/82, 87, 165, 95/220, 227, 228, 261; 210/656, 659, 198.2; 73/23.41, 23.35; 96/102, 105, 104

[56] References Cited

U.S. PATENT DOCUMENTS

| | | | |
|---|---|---|---|
| 2,494,427 | 1/1950 | Bidwell et al. | 55/203 |
| 2,705,053 | 3/1955 | Morris | 55/203 |
| 2,757,581 | 8/1956 | Freeman et al | 55/191 |
| 2,813,010 | 11/1957 | Hutchins | 23/232 |
| 3,063,286 | 11/1962 | Nerheim | 55/197 |
| 3,168,823 | 2/1965 | Reinecke et al. | 73/23.1 |
| 3,176,501 | 4/1965 | Briggs | 55/197 |
| 3,225,520 | 12/1965 | Burow | 55/67 |
| 3,529,405 | 9/1970 | Ashbrook | 55/191 |
| 3,728,845 | 4/1973 | Haruki et al. | 55/67 |
| 3,735,565 | 5/1973 | Gilby et al. | 55/197 |
| 3,800,946 | 4/1974 | Reid et al. | 55/191 |
| 3,964,884 | 6/1976 | Judith et al. | 55/192 |
| 3,999,963 | 12/1976 | Ririe, Jr. | 55/184 |
| 4,089,207 | 5/1978 | Patton | 55/27 |
| 4,098,592 | 7/1978 | Prescott et al. | 55/197 |
| 4,180,389 | 12/1979 | Paul | 55/28 |
| 4,201,555 | 5/1980 | Tkach | 55/191 |
| 4,231,256 | 11/1980 | Chapman et al. | 73/421.5 R |
| 4,510,056 | 4/1985 | Frykhult et al. | 55/191 |
| 4,617,031 | 10/1986 | Suh et al. | 55/203 |
| 4,666,476 | 5/1987 | Reeve et al. | 55/203 |
| 4,756,725 | 7/1988 | Badey et al. | 55/197 |
| 4,805,441 | 2/1989 | Sides et al. | 73/23.1 |
| 4,849,179 | 7/1989 | Reinhardt et al. | 422/89 |
| 4,998,433 | 3/1991 | Stumpf et al. | 73/25.01 |
| 5,014,541 | 5/1991 | Sides et al. | 73/23.41 |
| 5,028,243 | 7/1991 | Rubey | 55/197 |
| 5,036,710 | 8/1991 | King | 55/203 |
| 5,048,322 | 9/1991 | Hiller et al. | 73/23.41 |
| 5,065,614 | 11/1991 | Hartman et al. | 73/23.35 |
| 5,084,189 | 1/1992 | Richter | 55/191 |
| 5,250,093 | 10/1993 | Jiang et al. | 96/102 |
| 5,358,557 | 10/1994 | Jiang et al. | 95/82 |
| 5,470,380 | 11/1995 | Jiang et al. | 96/102 |

OTHER PUBLICATIONS

*Don't Water Down Your Analysis! Get A+ in Purge & Trap Performance: Tekmark® 2000Plus with the New Moisture Control Module,* Tekmar Company, Cincinnati, Ohio (1991) pp. 1–4.

(List continued on next page.)

Primary Examiner—Ernest G. Therkorn
Attorney, Agent, or Firm—Fish & Richardson P.C.

[57] ABSTRACT

A water management system removes water vapor from the analyte slug that is desorbed from the trap. The water management system includes a device having a passage through which the volatile organic chemicals and water pass, the passage being designed to remove water vapor by swirling action on the stream. The amount of water removed is more than can be accounted for by simple condensation. The invention also includes the adjustment of the temperature of the water management device during the sample concentration cycle to prevent undesired condensation prior to desorption.

13 Claims, 5 Drawing Sheets

OTHER PUBLICATIONS

Tekmar, *Optic Injector Price List*, pp. 1–2, (1994).

Tekmar Company, *An Optical View of Programmed Temperature Vaporization*; Cincinnati, Ohio Undated p. 1.

Tekmar Company, *Specifications and Pricing, OPTIC and OPTIC 600 Specification*; Cincinnati, Ohio p. 1 Undated.

*Applications and Technical Notes*; pp. 1–9 Undated.

Janssen, H.G. et al., Chromatography Technical Notes No. 1, *Large volume sample introduction in Capillary Gas Chromatography*; Ai Cambridge Ltd. Seminar, pp. 1–2 (1993).

Janssen, H.G., Chromatography Technical Notes No. 2, *Selecting the Injection Mode in Capillary Chromatography*; Ai Cambridge Ltd. Seminar, pp. 1–4 (1993).

Wyllie, S.G., et al., Chromatography Technical Notes No. 3, *Use of a temperature programmable injector in the static and dynamic headspace analysis of aroma volatiles*; Riva del Garda Symposium, Italy, pp. 1–4 (1993).

Jannsen, H.G., et al., Chromatography Technical Notes No. 5, *Analysing low volatility samples using high temperature PTV injection*; Ai Cambridge Ltd. Seminar, pp. 1–6 (1993).

Staniewski, J. et al., *Solvent Elimination Rate in Programmed Temperature Injections of Large Sample Volumes In Capillary GC*; 12th Int'l. Symposium on Capillary Chromatography, Japan, pp. 1–17 (1990).

Ridgeon, P.J., *A Universal Sample Introduction System for Capillary Columns*; Ai Cambridge Ltd. pp. 1–4 Undated.

Staniewski, J. et al., *Applicability of a Programmed Temperture Injector for Large Volume Sample Introduction in Capillary GC and for LC–GC Interfacing*; Fourteenth Int'l. Symposium on Capillary Chromatography, Baltimore, Maryland, pp. 654–662 (1992).

Hinshaw, J.V., *GC Troubleshooting, Programmed–Temperature Inlets*; IC–GC Int'l., vol. 5, No. 12, pp. 14–16 Undated.

Perkins, R., *The Use of PTV injection to enhance analytical Performance*; Tekmar Program of Seminars, Pittcon, (1994).

Tekmar Brochure, *2000 Series Concentrator Systems . . . for Volatile Organics Analysis by Purge and Trap or Dynamic Headspace*; Cincinnati, Ohio pp. 1–8 Undated.

Tekmar Brochure, *3000 Purge and Trap Concentrator*, Tekmar Company, Cincinnati, Ohio, pp. 1–16 Undated.

Chemical Data Systems, *CDS 380 Automated Purge and Trap System*; Oxford, PA (1988) pp. 1–4.

Chemical Data Systems, *CDS 330 GC Sample Concentrator, Programmed Cryo–Focusing Optimized for Direct* Capillary GC; Oxford, PA (1985) pp. 1–8.

Chemical Data Systems, *Model 330 Trapping Concentrator*; Oxford, PA (1988) pp. 1–3.

Chemical Data Systems, *Model 350/380 Autosampler*; Oxford, PA (1988) p. 1.

O.I. Analytical, *Efficiency of Cryo–Focusing Traps for Purge–And–Trap Gas Chromatography*, Application Note 04040195; New Orleans, LA (1992) pp. 1–4.

O.I. Analytical, *GC/MS Analysis of Volatiles in Less Than 15 Minutes!*, Application Note 05250295; ChromConnection Newsletter (Jun., 1993) pp. 1–4.

O.I. Analytical Applications News 1992, Newsworthy, No. 0430493, *Use of a Cryo–Focusing Module™ as a Water Management Tool in Purge–And–Trap/GC/MS Analysis*; New Orleans, La., pp. 1–25 (1992).

Allen K. Vickers, *An Automated Purge–and–Trap System for Analyzing Volatile Organic Compounds in Drinking Water*; O.I. Analytical Applications News 1991, Newsworthy, No. 02211091 (1991) p. 1

Alltech Environmental Update, *Volatile Organics Analysis: Building a State–of–the–Art Purge and Trap GC/MS System*; O.I. Analytical Applications News 1991, Newsworthy, No. 02970691 (1991) pp. 1–8.

Ho, J.S., et al., *A Fully Automated Purge–and–Trap System for Analyzing Volatile Organics in Drinking Water*; O.I. Analytical Applications News 1991, Newsworthy, No. 03330493 (1991) p. 1.

O.I. Analytical Applications News 1991, Newsworthy, No. 03750991, *The Compatibility of the OI Analytical Purge and Trap with the HP 5971A MSD*(1991) pp. 1–4.

J&W Scientific, GC Environmental Application Note #E3, *EPA 524.2 (Revision 4) With Extraordinary Speed and Resolution, 0 to 84 in 27.2!* (1994) pp. 1–4.

*Tekmar® Model 1000 Capillary Interface*; Tekmar Company, Cincinnati, Ohio pp. 1–4 Undated.

Tekmar, *What is Optic!, Advantages of Optic*; Tekmar Company, Cincinnati, Ohio p. 1 Undated.

Tekmar, *Primary Users, Applications*; Tekmar Company, Cincinnati, Ohio p. 1 Undated.

Tekmar 3 x 5 card, "*Can You Make The Grade!*", *Purge and Trap Report Card*Tekmar Company, Cincinnati, Ohio pp. 1 & 2 Undated.

Westendorf, R.G., *Design and performance of a microprocessor–based purge and trap concentrator*; American Laboratory, pp. 66–73 (1987).

Westendorf, R., *Managing Water in Purge & Trap GC/MS*; Environmental Lab, pp. 36–39 (Aug./Sep. 1992).

Applications News 1992, Newsworthy, No. 0420493, *OI Analytical Model 4560 Sample Concentrator—Cyclone Water Management™ System*; O.I. Analytical, College Station, Texas (1992) pp. 1–2.

*Don't Water Down Your Analysis?, Tekmar 2000 Plus Purge and Trap™ Concentrator with Moisture Control Module*; Tekmar Company, Cincinnati, Ohio p. 56 Undated.

Twachtman, J., *Form Letter Regarding 2000 Series*; Tekmar Company, Cincinnati, Ohio (Apr., 1992) pp. 1.

*Don't Water Down Your Analysis?, Get A+ in Purge & Trap Performance; Tekmar® 2000 Plus with the New Moisture Control Module*; Tekmar Company, Cincinnati, Ohio pp. 1 & 2 Undated.

Sensel, A.K., et al., *Comparison of a Narrow Bore Column with a Cryofocusing Module™ and a Wide Bore Column with Jet Separator for EPA Method 524.2*; 1991 Pittsburgh Conference, Tekmar Company (1991) Pittsburgh Conference, Tekmar Company (1991) pp. 1–16.

Applications News 1992, Newsworthy, No. 04050593, *Theory and Operation of Water Management Methods in Purge–and–Trap Gas Chromatography*; O.I. Analytical, College Station, Texas (1992) pp. 1–6.

*1996 HP Environmental Solutions Catalog*; Hewlett Packard Company, pp. 1–120 (1995).

*GC Star ● CX Series*, Varian (1993) pp. 1–3.

*External Carrier Module User's Manual*; O.I. Analytical, College Station, Texas, pp. i–7 Undated.

Hewlett–Packard, *Peak News for Users of Analytical Instrumentation*; United States, No. 1 (1995) pp. 1–5.

*External Carrier Module*; O.I. Analytical, College Station, Texas Undated pp. 1 & 2.

*Varian's 3300 and 3400 Gas Chromatographs*; Undated pp. 1–3.

Abeel, S.M., et al., *Trends in Purge and Trap*; Journal of Chromatographic Science, vol. 32 (1994) pp. 328–338.

*4460A Concentrator System Performance Attributes*; O.I. Analytical, College Station, Texas pp. 1 & 2 Undated.

O.I. Analytical, Application Note 05181195, *Cycle Time as a Productivity Factor in Purge–and–Trap Analysis*; O.I. Analytical, College Station, Texas pp. 1 & 2 Undated.

Snelling, R.D., et al., *A New Purge and Trap Sample Concentrator Optimized for Low Desorb Flow Operation*O.I. Analytical, College Station, Texas (Mar. 2, 1996) pp. 2–6.

Riga, T.J., *Low Level Analysis of 524.2 Analytes Using a 3000 Purge and Trap and a Varian Direct Split Interface*; TekNOTE, Tekmar Company, Cincinnati, Ohio (1994) pp. 1–4.

Hollis, J.S., et al., *Method 524.2 By Capillary Direct Via The Split/Splitless Injection Port on the Hewlett–Packard 5890/ 5971 GC/MS*; 220P pp. 2–10 Undated.

Neal, B., *EPA Volatiles Analysis Using Narrow Bore Capillary Columns*; Hewlett Packard Company pp. 1–11 Undated.

*EPA Method 524.2 by capillary direct split mode using the HP 5972A Mass Selective Detector (MSD)*; Hewlett–Packard Applications Group, MS Application Guide, HP 5972A, MS 94–5 (1994) pp. 3–6.

Bayer, C.W., et al., *Sampling and analysis techniques for trace volatile organic emissions from Consumer Products*; Journal of Chromatographic Sciences, 26:168–173 (1988).

Ashley, D.L., et al., *Determining volatile organic compounds in human blood from a large sample population by using purge and trap gas chromatography/mass spectrometry*; Anal. Chem. 64:1021–29 (1992).

Saucer, T.C., *Volatile Liquid hydrocarbon characterization of underwater hydrocarbon vents and formation waters from offshore production operations*; Enivron. Sci. & Techol., 15(8):917–923 (1981).

Hall, P.M., *Analysis of aldehydes desorbed from an aluminum surface dynamic headspace gas chromatography—mass spectrometry*; LC–GC 7(1):52–57 (Jan. 1989).

*Organic Volatile Impurities*; Pharmacopeial Forum 19(2):4917–20 (Mar./Apr. 1993).

Page, B.D., et al., *Survey of Bottled Drinking Water Sold in Canada. Part 2. Selected Volatile Organic Compounds*; Journal of AOAC Int'l., vol. 76, No. 1, pp. 26–31 (1993).

Eichelberger, J.W., et al., Method 524.2, Revision 3.0, *Measurement of Purgeable Organic Compounds in Water by Capillary Column Gas Chromatography/Mass Spectrometry*; Environmental Mon Sys. Lab., pp. 285–323 (1989).

Method 502.2.: *Volatile Organic Compounds in Water by Purge and Trap Capillary Column Gas Chromatography With Photoionization and Electrolytic Conductivity Detectors in Series*; (Sep. 1986) pp. 1–27.

Method 524.1: *Volatile Organic Compounds in Water by Purge and Trap Gas Chromatography/Mass Spectrometry*; pp. 56–81.

Method 5030B, Revision 2: *Purge–And–Trap for Aqueous Samples*; 1–21, Revision 2 (Jan. 1995).

Method 503.1.: *Volatile Aromatic and Unsaturated Organic Compounds in Water by Purge and Trap Gas Chromatography*; pp. 28–55 Undated.

Method 8020: *Aromatic Volatile Organics*; pp. 8020–1–8020–13, Revision 0 (Sep. 1986).

Method 8020A, Revision 1: *Aromatic Volatile Organics by Gas Chromatography*; pp. 8020A–1–8020A–14 (Sep. 1994)

*Purgeable Aromatics—Method 602*; Environmental Monitoring and Support Laboratory, EPA Test Method, U.S. Environmental Protection Agency, Cincinnati, Ohio, pp. 602–1–602–10 (Jul., 1982).

*Acrolein and Acrylonitrile—Method 603*; Environmental Monitoring and Support Laboratory, EPA Test Method, U.S. Environmental Protection Agency, Cincinnati, Ohio, pp. 603–1–603–8 (1982).

*Method 8030: Acrolein, Acrylonitrile, Acetonitrile*pp. 8030–1–8030–10, Revision 0, (Sep. 1986).

*Supleco Catalog*; Supelco, Inc., Bellefonte, PA, pp. i–960 (1995).

*VICI Valco Instruments Co., Inc. Catalog*; Valco Instruments Co., Inc., Houston, Texas, pp. 2–60 (1991).

*Guide to Environmental Analytical Methods, 2d Edition*; O.I. Analytical, College Station, Texas, pp. iii–F–1 (1992).

*Purge and Trap Comparisions*; O.I. Analytical, College Station, Texas, pp. 1–2 (1996).

Snelling, R.D., et al., Abstract No. 022P, *A New Purge–And–Trap Sample Concentrator Optimized for Low Desorb Flow Operation*; presented at 1996 Technical Program, Pittsburg Conf. 96, Session 165, pp. 20 (Mar. 3, 1996).

Snelling, R.D., et al., Abstract No. 1125, *Detection Limits for Purge and Trap–Gas Chromatography Spectrometry Using a Purge–And–Trap Sample Concentrator Optimized for Capillary Column Flow Rates*; presented at 1996 Technical Program, Pittsburg Conf. '96, Session 136, pp. 64 (Mar. 3, 1996).

*Hypodermic Size Tubing, Section III, The MicroGroup Products and Services Specifiers Guidebook*; All–Tube Corporation, Medway, MA, pp. 27, 67, 30, 7119, 24 Undated.

CDS 330 GC–Sample Concentrator, *Glass–Lined Option Improves and Simplifies GC Analysis of Polar and Labile Compounds*; Chemical Data Systems, Oxford, PA (1985).

*4460A Sample Concentrator System*, OI Analytical, pp. 1 through 7 Undated.

*4460A Purge and Trap Sample Concentrator*, OI Analytical, pp. 1 and 2 Undated.

*OI Analytical Analyzers, Model 4460A Purge and Trap Sample Concentrator*, Technical News 1990 Newsworthy, No. 00860690, pp. 1 Undated.

*OI Analytical Analyzers, Model ASM and MPM–16 for the 4460A Purge and Trap Sample Concentrator*, Technical News 1990 Newsworthy, No. 0880690, p. 1 Undated.

*Advantages of Advanced 4460A Purge & Trap Design*, Applications News 1990, Newsworthy No. 00940690, p. 1 Undated.

*Model 4460A Purge and Trap Degradation/Contaminant Peak Solution*, Technical News 1990, Newsworthy, No. 01100790, p. 1 Undated.

*4460A Concentrator System Performance Attributes*, OI Analytical, pp. 1 and 2 Undated.

*Volatile Organics Analysis: Building a State–of–the–Art Purge and Trap GC/MS System*, Applications News 1991, Newsworthy, No. 02970691, pp. 1 through 8 Undated.

*A Fully Automated Purge–and–Trap System for Analyzing Volatile Organics in Drinking Water*, Applications News 1991, Newsworthy, No. 03330493, Jul. 1989, pp. 1 through 9.

*The Analysis of Volatile Organics in Drinking Water with an OI 4460A Purge and Trap and an HP GC/MS System*, Applications News 1992, Newsworthy, No. 03610992, Aug., 1991, pp. 1 through 6.

*The Compatibility of the OI Analytical Purge and Trap with the HP 5971A MSD*, Applications News 1991, Newsworthy, No. 03750991, pp. 1 through 4 Undated.

*An Automated Purge–and–Trap System for Analyzing Volatile Organic Compounds in Drinking Water*, Applications News 1991, Newsworthy, No. 02211091, May 1991, pp. 1 through 5.

*Don't Water Down Your Analysis!*, Tekmar®, pp. 1 and 2 Undated.

Westendorf, *Design and Performance of a Microprocessor- -based purge and trap concentrator*, Tekmar, 66–73 (Oct. 1987).

*Tekmar 2000 Plus Purge and Trap™ Concentrator with Moisture Control Module*, p. 56 Undated.

*The ALS 2016 Automatic Sampler*, pp. 49 and 50.

*Perry's Chemical Engineers' Handbook* (*Fourth Edition*), McGraw–Hill, 1969, pp. 11–15 and 11–16.

Giese, R.W., et al.; Adsorption/thermal desorption for the determination of volatile organic compounds in water; *Journal of Chromatography*; 537:321–328 (1991).

Rosen, Michael Elliott: The Development of Adsorption/Thermal Desorption for the Determination of Trace Levels of Volatile Organic Compounds in Groundwater: Dissertation submitted to the faculty of the Oregon Graduate Center in partial fulfillment of the requirements for the degree Doctor of Philosphy in Environmental Science and Engineering: (1988) pp. VI–XXV and 1–70 and 245–252.

Johnson, Eric, et al. *Efficient Water Removal for GC/MS Analysis of Volatile Organic Compounds with Tekmar's Moisture Control Module*, Tekmar Company (1990).

Barber, Michael T., *Recent Advances in Volatile Organic Analysis Using Gas Chromatography/ Mass Spectrometry: Drinking Water Analysis on the INCOS™ 500*, Finnigan MAT (1990).

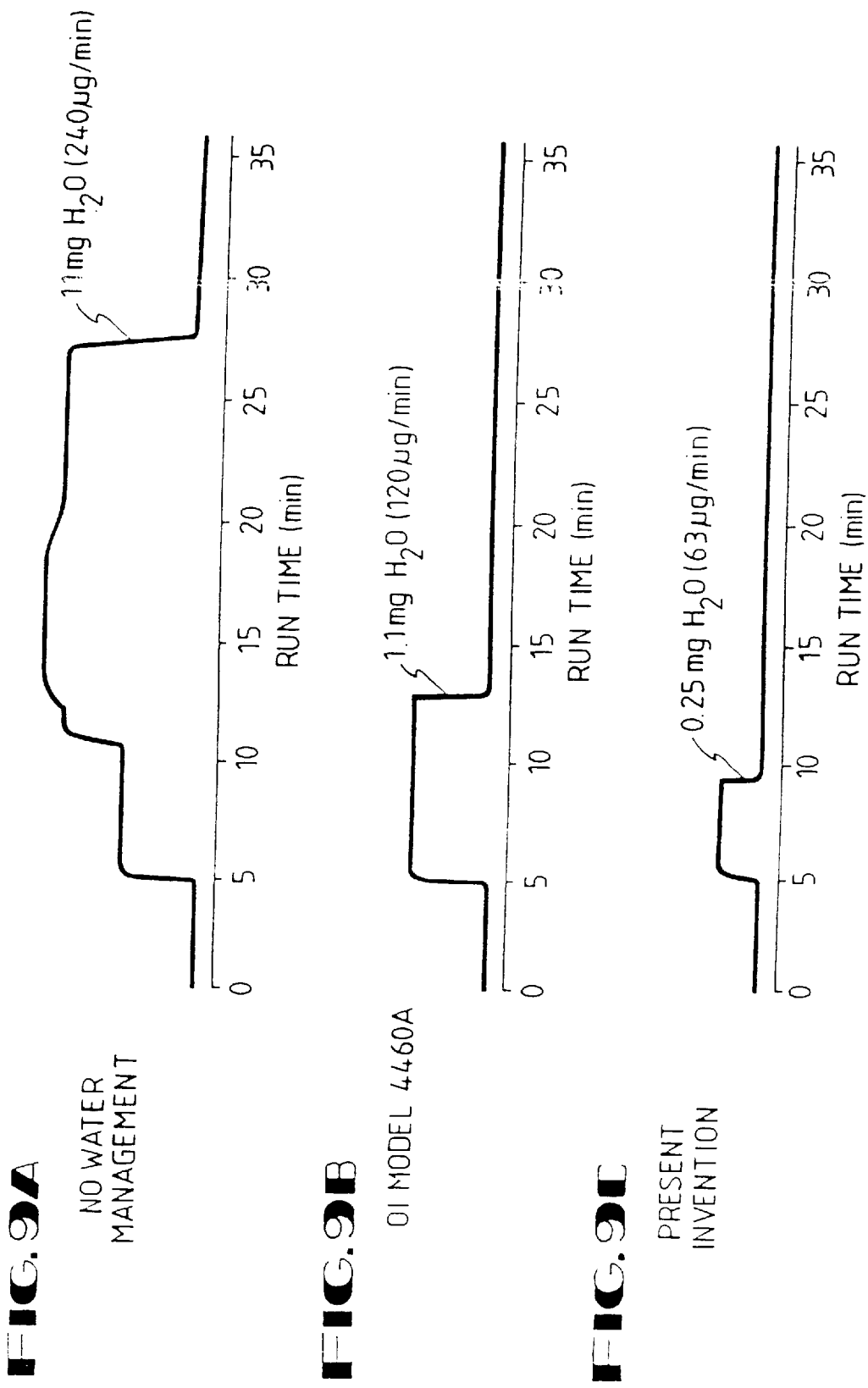

WATER MANAGEMENT DEVICE FOR GAS CHROMATOGRAPHY SAMPLE CONCENTRATION

This is a continuation of application Ser. No. 08/562,840, filed Nov. 27, 1995, now U.S. Pat. No. 5,582,633; which is a continuation of application Ser. No. 08/282,171, filed Jul. 29, 1994, now U.S. Pat. No. 5,470,380, which was a divisional of application Ser. No. 08/061,986, filed May 14, 1993, now U.S. Pat. No. 5,358,557; which was a divisional of application Ser. No. 07/848,395, filed Mar. 9, 1992, now U.S. Pat. No. 5,250,093.

BACKGROUND OF THE INVENTION

1. Field of the Invention

The present invention relates generally to sample concentration for analyzing volatile organic compounds in air, water and soils. More particularly, the invention involves a device for removing water vapor from the analyte slug as it is carried from the trap of the sample concentrator to the gas chromatographic column.

2. Related Art

Sample concentrators are used in purge-and-trap, headspace, and thermal desorption gas chromatography ("GC") analysis. Purge-and-trap GC technique has been used for analyzing volatile organics in water since approximately the early 1970's. In 1987 the U.S. Environmental Protection Agency ("EPA") promulgated national primary drinking water regulations for certain volatile organic chemicals ("VOCs"). The EPA also proposed maximum contamination levels for eight volatile organic chemicals. These regulations require the use of the purge-and-trap GC technique. In addition to the eight regulated volatile organic chemicals, the EPA also promulgated monitoring requirements for an additional 52 synthetic volatile organic chemicals.

The EPA has approved certain analytical methods for analyzing these 60 compounds. One of the methods is 502.2, a purge-and-trap capillary-column GC method using a photoionization detector and an electrolytic conductivity detector joined in series. A second method is method 524.2, a purge-and-trap capillary-column GC-MS method.

Purge-and-trap systems for analyzing VOCs in drinking water have been assembled from a variety of equipment typically including a purging device, trap, and desorber. These systems also are referred to as sample concentrators. The purge-and-trap system or sample concentrator interfaces to a GC capillary column, then with a photoionization detector/electrolytic conductivity detector or a mass-spectrometer. These components are interconnected via pneumatic conduits.

Highly volatile organic compounds with low water solubility are extracted (purged) from the sample matrix by bubbling an inert gas (i.e., helium or nitrogen) through a five milliliter aqueous sample. Purged sample components are trapped in a tube containing suitable sorbent materials. When purging is complete, the sorbent tube is heated and backflushed with the inert gas to desorb trapped sample components onto a capillary GC column. The column is temperature programmed to separate the method analytes which are then detected with a photoionization detector (PID) and a halogen specific detector placed in series, or with a mass spectrometer.

Tentative identifications are confirmed by analyzing standards under the same conditions used for samples, and comparing results and GC retention times. Additional confirmatory information can be gained by comparing the relative response from the two detectors. Each identified component is measured by relating the response produced for that compound to the response produced by a compound that is used as an internal standard. For absolute confirmation, the gas chromatography/mass spectrometry (GC/MS) determination according to method 524.1 or method 524.2 may be used.

As stated above, the typical purge and trap system consists of the purging device, trap, and desorber. Systems are commercially available from several sources that meet EPA specifications.

Under EPA specifications, the glass purging device must be designed to accept five to twenty-five ml. samples with a water column at least 5 cm. deep. Gaseous volumes above the sample are kept to a minimum to reduce "dead volume" effects. The purged gas passes through the water column as finely divided bubbles.

The sorbent trap is a tube typically at least 25 cm. long and having an inside diameter of at least 0.105 inches. The trap contains certain sorbent materials which the EPA has specified as 2,6-diphenylene oxide polymer, silica gel, and coconut charcoal. The EPA regulations specify the ratios of the adsorbent material. The desorber must be capable of rapidly heating the trap to 180° C.

The model 4460A sample concentrator manufactured by OI Analytical of College Station, Tex., is an example of a purge and trap, or sample concentrator, device. The model 4460A is a microprocessor controlled device that stores method 502.2 and 524.2 operating conditions as default parameters. Operating conditions may be changed by the user to accommodate other types of purge and trap analysis.

In addition to purge-and-trap methods and analyses, sample concentration gas chromatography is used in headspace analysis of liquids and solids, and in thermal desorption analysis of air tube samples. Headspace and thermal desorption techniques are not only used for environmental analyses, but also for clinical and industrial applications.

During all sample concentration GC analysis, some amount of water is purged from the sample and caught in the trap along with the compounds of interest. This is a problem encountered in the prior art. A typical rate of water transfer is 1 microliter per minute of purge time. Without any water management system, during the 11-minute purge time required by method 502.2, approximately 10 to 11 microliters of water are transferred to the trap. This water transfer as a function of time is represented in FIG. 9. When the trap is heated, the VOCs and the water vapor are desorbed into the GC column. The presence of water vapor in the capillary column has many detrimental effects including shifts of analyte retention times, the quenching of PID response, deterioration of the nickel reaction time in the ELCD, and the suppression of quantification ion response in a mass spectrometer. Along with trapped water, there also may be trapped methanol causing deleterious effects on the separation and detection of VOCs.

FIGS. 1 and 2 are examples of plots showing how water transfer affects ion response of a GC or mass spectrometer ("MS"). The units on the horizontal axis are minutes of GC run time, and the units on the vertical axis are indicative of the abundance of each analyte.

FIG. 1 represents a GC or MS response sensitive to water as well as the analytes of interest. Water transfer during approximately the first six or seven minutes is represented on this plot as a "plateau" during that period. Thus, detection of analytes is difficult during that period.

FIG. 2 represents the same analysis as that of FIG. 1, except the GC or MS is sensitive only to an ion range excluding water. Despite the absence of the plateau from FIG. 1, water transfer during approximately the first six or seven minutes tends to diminish or obscure the peaks of interest during that period. Typically, peaks are lower due to the presence of water vapor. Therefore, the plot of FIG. 2 similarly presents analyte detection problems because of the water transfer problem.

Typically, the methods described above call for a 4 minute desorb period, which is represented on the GC or MS plot as the first 4 minutes of run time. Generally, few if any analytes show up on the GC or MS during approximately the first 4 minutes. However, methane and water begin appearing during that period. After the four minute desorb period, water continues to appear, obscuring the analytes of interest.

Water continues to be transferred from the trap to the GC during the remainder of the run time, or will be limited to approximately the first 6 or 7 minutes of run time, depending on various factors. In general, if water transfer time is reduced, there is greater distortion of results (represented graphically as a "higher" plateau) during that reduced time period. If the water transfer time is extended, the distortion will continue further during the GC run time. Regardless of the length of time during which water transfer occurs, it has a tendency to obscure the analytes of interest.

Devices in the prior art addressing the water transfer problem have involved placing a condenser in line between the trap and GC. However, removing water vapor by condensation has certain disadvantages. One disadvantage is "dead volume," which has deleterious effects on the GC analysis. Due to dead volume, volatile compounds are trapped in the condenser, and GC peaks exhibit "tailing."

Another disadvantage of the condensation approach is that passing of the compound through a cold zone in the condenser interrupts the desired flow of the compound to the GC column. Retention times for analytes are less predictable and repeatable, and a fraction of the analyte may be retarded in the cold zone, reducing the ability to detect and quantify certain compounds. Further, it is desirable to heat the pneumatic lines so that condensation does not occur.

In the OI Analytical model 4460A sample concentrator, the desorption of water vapor onto the GC column is reduced by a water management system that utilizes rapid trap heating at 800° C. per minute coupled with an expansion/condensation chamber that allows only 0.25 microliters per minute of water vapor to desorb onto the GC column. Due to this water management system, over 90% of the trapped water can be rejected. When the chamber is at 35 degrees C., approximately 1.1 microliters of water vapor are desorbed onto the GC column during the 4 minute desorb period. The GC response to water vapor only as a function of time is shown if FIG. 9. The same device at 25 degrees C. delivers approximately 0.93 microliters of water to the GC column. This feature is particularly valuable in detection and measurement of some early eluting compounds whose PID, ELCD or MS responses are normally attenuated by transfer of water vapor to the detector. These systems also reduce water-activated deterioration of the ELCD nickel reaction tube and the subsequent loss of response to certain compounds.

Another example of a condensor-type device is the TEK-MAR 2000 Plus purge and trap concentrator, with a moisture control module ("MCM"). The MCM condensate trap cools the VOCs and water that pass through, then preheats the sorbent trap. Upon reaching the preheat temperature, the trap is backflushed with carrier gas sweeping the volatiles and water from the heated trap over to the cooled MCM condensate trap. The water condensed from the gas stream is isolated from the carrier gas flow path, and then is heated to vaporize through a vent. A thermoelectric module (Peltier effect module) is used to cool and heat the MCM in an effort to remove the water vapor from the analyte stream. The Peltier effect module passes electric current through the junction of two thermoelectric materials to cool the MCM, and then to subsequently heat it to remove the water vapor. However, the Peltier module is susceptible to failure after repeated heating and cooling cycles. In addition, the cost of the MCM unit and the electrical requirements are disadvantages of such a water management system.

As another alternative to eliminate water vapor transfer to the GC column, OI Analytical's Anhydrator reduces water transfer to the GC column to less than 0.004 microliters per minute. The Anhydrator consists of Nafion tubing available from Perma-Ture Corporation. The Anhydrator has disadvantages and problems including the irreversible loss of polar analytes such as acetone and methanol, which are removed along with the water.

SUMMARY OF THE INVENTION

The present invention overcomes the above-mentioned problems and disadvantages by providing a water management system wherein the amount of water vapor removed is greater than what can be accomplished by vapor pressure and temperature behavior. The amount of water removed is more than can be accounted for by simple condensation.

The invention includes a water management device having a passage through which VOCs and water vapor pass, the passage designed to remove water vapor by swirling action on the stream. The passage has additional surface area, such as an internally threaded configuration, without significantly increasing the dead volume, and without temperatures as low as the prior art.

The invention also includes a process of adjusting the temperature of the water management device during the purge, desorb, and bake cycle. During the purge step, the device reaches a temperature somewhat higher than the trap temperature, to reduce condensation before the analyte stream reaches the trap. Just prior to desorb, the water management device is cooled further, approaching ambient room temperature, to remove water vapor from the analyte stream being desorbed from the trap to the GC.

BRIEF DESCRIPTION OF THE DRAWINGS

FIG. 9A, 9B, and 9C are a typical GC or MS response sensitive only to water, for volume of water transfer as a function of time, comparing water transfer to the GC without any water management system, with the OI Analytical Model 4460A, and with the present invention.

DETAILED DESCRIPTION OF THE PREFERRED EMBODIMENT

Figure 7:
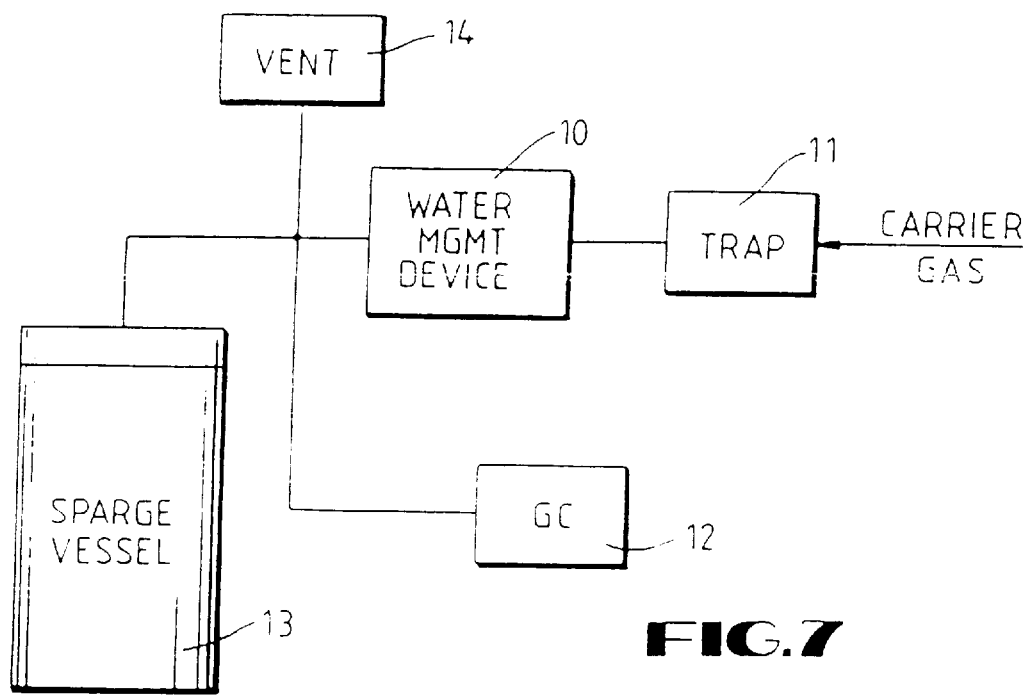
FIG. 7 is a schematic diagram of the water management device of the present invention and the other components used in a typical sample concentration/GC system.

In a preferred embodiment, water management device 10 may be interposed in the pneumatic line between the trap 11 and GC 12, as shown in FIG. 7. Also shown in FIG. 7 is a sparge vessel 13, vent 14, and pneumatic tubing 15 connecting the components.

Typically, the sample concentration cycle involves the steps of purge, desorb, and bake. During purge, the analyte stream flows from sparge vessel 13 through water management device 10 to trap 11, which is at a cool temperature (approximately 20 degrees C.). During desorb, the trap is heated (to approximately 180 degrees C.) and backflushed with carrier gas. The analyte stream flows from the trap to the water management device and then to the GC or MS. During bake, both the trap and the water management device are heated (to approximately 240 degrees C.). Dry gas is introduced to the system to move water vapor out of the water management device and trap through vent 14.

Although a preferred embodiment of this invention is intended for desorb by back-flush of the trap 11, it is contemplated that the invention may also be used with a fore-flush of the trap.

Now referring to FIGS. 3–6, a preferred embodiment of the water management device 10 is shown. In this embodiment, the invention comprises a stainless steel body portion 20 preferably having an L-shaped configuration. The body portion is gold plated. A passage or bore 31 extends through the body 20, from a first end 32 to a second end 33. The bore 31 has a first section 34 adjacent the first end, and a second section 35 adjacent the second end. The first and second sections of the bore meet at intersection 16, preferably at an angle of approximately ninety degrees.

As stated above, the present invention is primarily intended for use with a back-flush system, but also may be used with a fore-flush system. When used in a back-flush system, the first end of the device is the outlet during purge and the inlet during desorb, and the second end is the inlet during purge and the outlet during desorb. The removal of water is intended to take place primarily during the desorb step, which will be discussed below.

In desorb, the analyte stream from the trap 11 enters the first section 34 of the bore, which has a stepped diameter and a total length of approximately 1.000 inches. Starting from the first end 32, the first section 34 of the bore is internally threaded at 41 to provide a fitting body for engagement with a nut (not shown) and pneumatic tubing, which is then connected to trap 11. Adjacent the first end, a portion of the internally threaded portion 41 has a conical shape 42 for mating with a ferrule (not shown) on the pneumatic tubing. Instead, external threads may be used if desired.

Still referring to first section 34 of the bore, in a preferred embodiment threads 41 terminate at 43, and the bore has an internal diameter of 0.125 inches. This internal diameter can be varied depending on various factors such as the flow rate desired, the pneumatic tubing and the trap used in the system, and the inner diameter of the GC column used. This diameter is preferred for use with pneumatic tubing having an internal diameter of 0.03 inches, a trap having an internal diameter of 0.105 inches, and GC column internal diameters ranging from approximately 0.010 to 0.020 inches.

In a preferred embodiment shown in FIGS. 3–6, the first section 34 includes internal shoulder 44 and a reduction in the bore to 0.080 inches, as shown at neck 45. The reduction in diameter from 0.125 to 0.080 tends to increase the velocity of the analyte stream flowing through the bore. The neck 45 has an axial length of 0.10 inches and intersects the second section 35 of the bore at intersection 16.

Figure 1:
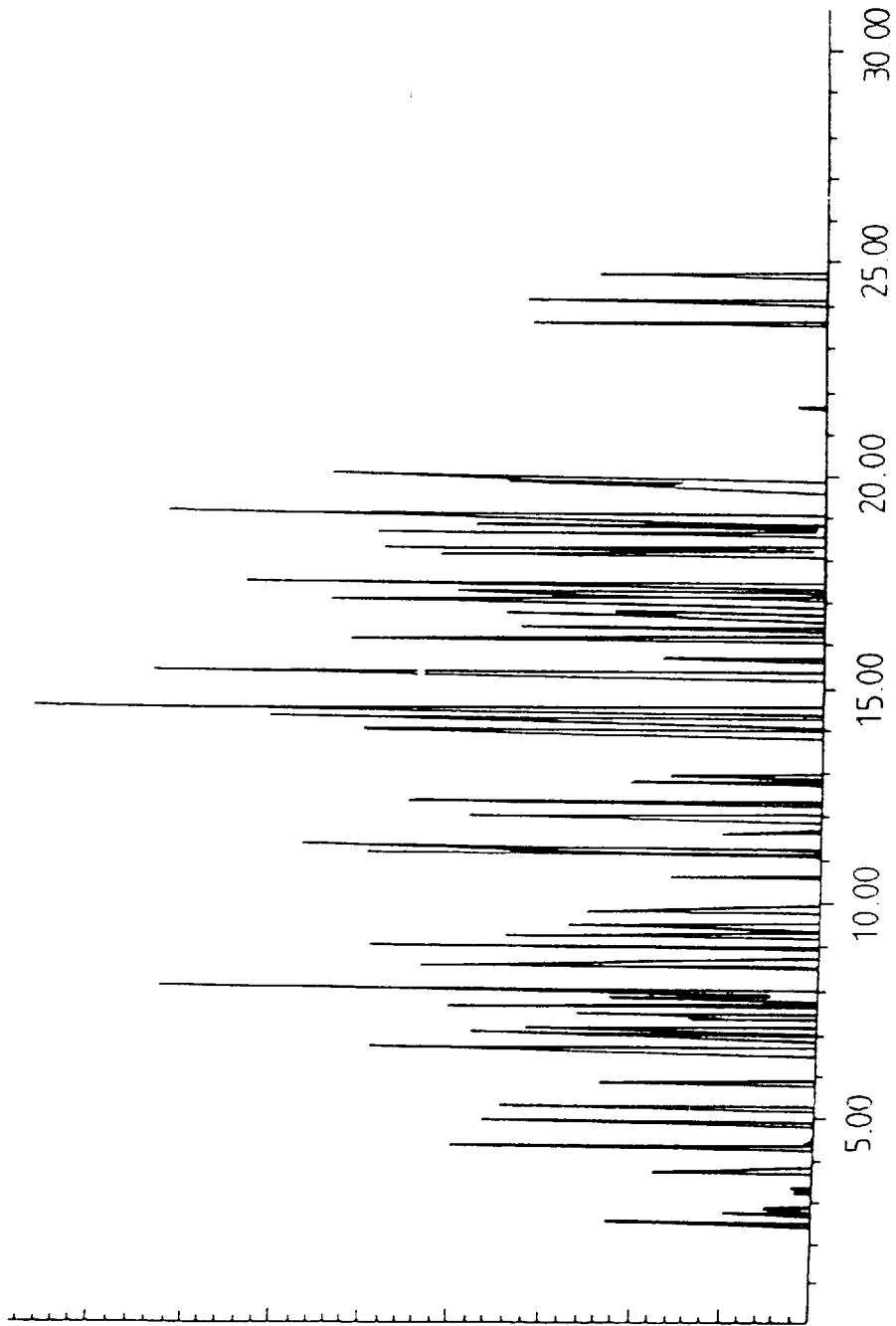
FIG. 1 is a typical GC or MS response sensitive to water and the analytes of interest, showing the detrimental effect of water transfer without the present invention.
Figure 2:
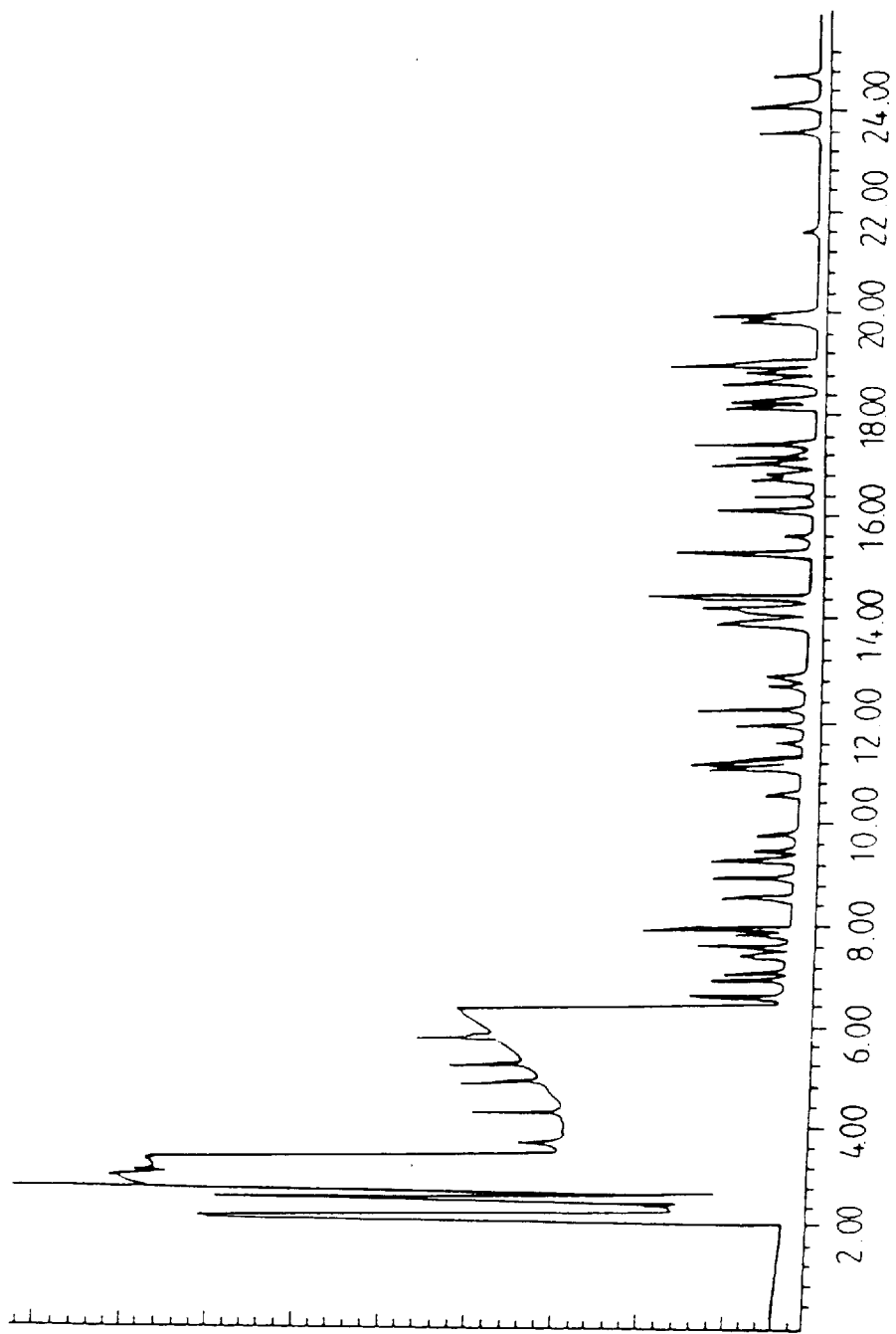
FIG. 2 is a typical GC or MS response sensitive only to an ion range excluding water, showing the detrimental effect of water transfer without the present invention.
Figure 4:
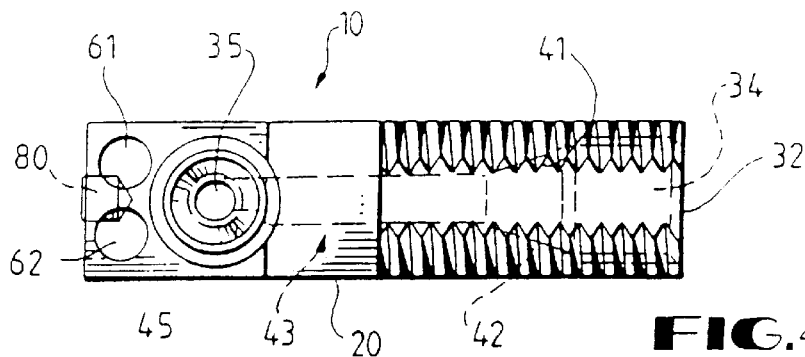
FIG. 4 is a top view, in section, of the water management device shown in FIG. 3.
Figure 5:
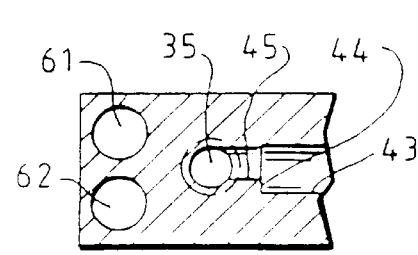
FIG. 5 is a section view taken along section line 5 of FIG. 3, showing the neck between the first and second sections of the bore in the water management device.
Figure 3:
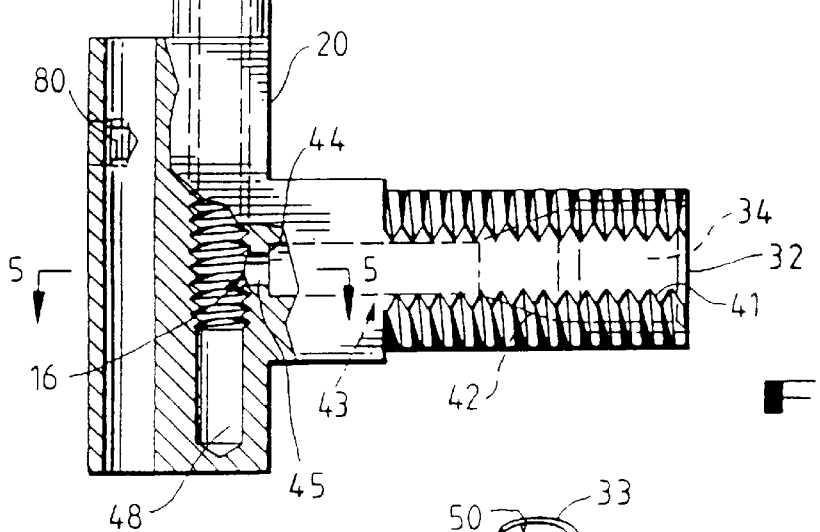
FIG. 3 is a side view, partially in section, of the water management device according to the present invention.

In a preferred embodiment the first and second sections of the bore intersect at an angle of ninety degrees. As shown in FIG. 5, the neck 45 is off-center from the center line of the first section of the bore, and is similarly off-center from the second section of the bore, as will be explained in more detail below.

The second section 35 of the bore has an internal diameter of 0.110 inches. The second section forms a T with the first section, with the one leg extending down to reservoir 48. Water vapor that is caught in the second portion of the bore drains downwardly into the reservoir 48 and remains there until the bake step in the cycle. Thus, the water management device should be aligned such that water will drain into the reservoir. Preferably, the second section of the bore is vertically aligned.

The reservoir is considered "unswept volume" or "dead volume" in the system, as the analyte stream will normally bypass that volume. The reservoir 48 has an axial length of about 0.280 inches and a volume of approximately 40 to 50 microliters. The volume of the reservoir may be varied depending on the maximum volume of water that will be removed from the analyte stream as it passes through the second section of the bore. However, it is contemplated that the reservoir volume should not be significantly below about 10 microliters because it would be insufficient for the anticipated water volume, or above about 100 microliters because of deleterious effects of "unswept volume" or "dead volume" on the system.

The second section 35 also is configured such that the "dead volume" is minimized. An internal diameter of 0.110 inches is most preferred for second section 35, which is primarily intended for use with GC columns having internal diameters of between approximately 0.010 and 0.020 inches. It is contemplated that the internal diameter of the second section should be no greater than approximately 11 times the internal diameter of the GC column.

In a preferred embodiment, the second section of the bore is internally threaded. This geometry results in a swirling effect on the analyte slug as it leaves the first section and enters the second section, to remove more water vapor from the analyte slug than would be expected at a given temperature and pressure. Preferably, the length of the internally threaded portion 49 is 1.080 inches. It is contemplated that the length of this portion will be approximately ten times the diameter of the second section.

Although a threaded configuration is shown for the second section, other non-smooth geometries may be used to remove water vapor and cause that water vapor to be trapped in the second section of the bore. For example, a series of ridges may be included in the interior surface of the second section. Alternatively, the second section of the bore may be conical in configuration. As with the threaded or ridged configuration, the conical shape causes a swirling effect on the water vapor to remove that vapor from the analyte slug.

As discussed above, the neck 45 is off-center from the second section 35 of the bore. This can be seen in FIG. 5.

This arrangement enhances the swirling effect because of a tangential feed to the second section of the bore. Further, the neck's internal diameter is smaller than the diameter of the second section of the bore. Thus, the analyte stream loses heat due to expansion upon entering the second section of the bore.

The second section of the bore has a total length of preferably about 1.600 inches. Adjacent the second end is a conical portion 50 for engagement with a ferrule or other connection (not shown). Also shown adjacent the second end are external threads 51 for engagement with a fitting and pneumatic tubing, which is then connected to GC 12 and vent 14.

As discussed above, water vapor that is removed from the analyte slug drains into reservoir 48 and accumulates therein. During the bake step, the water in reservoir 48 may be removed.

The configuration of the water management device is such that the amount of water vapor removed is above what one would expect to be accomplished from condensation. A number of different geometries for the second section are contemplated, including those having an irregular shaped surface or non-cylindrical shape. In contrast, the prior art has generally specified that the pneumatic tubing and passageways between the trap and GC are smooth-walled.

In the prior art, i.e. the OI Analytical Model 4460A, at 35 degrees C. approximately 1.1 microliters of water vapor are desorbed onto the GC column during the 4 minute desorb period. Because of normal condensation, only approximately 0.93 microliters of water would be delivered to the GC column if the temperature was reduced to 25 degrees C. However, at the same temperature of 25 degrees C., the present invention reduces the amount of water delivered to the GC column much further, to approximately 0.25 microliters. Thus, the present invention substantially reduces the amount of water transfer at a given temperature.

The water management device of the present invention includes a pair of bores 61, 62 adjacent the second section. Bore 61 is for insertion of a heating cartridge (not shown), which is preferably of between 50 and 100 watts. Bore 62 is for a thermocouple (not shown), preferably a Type K. The heating cartridge and thermocouple are functionally connected to an electrical power source (not shown) for heating the water management device, and monitoring its temperature. The heating cartridge and thermocouple are anchored to the water management device body with set screw 80.

Figure 6:
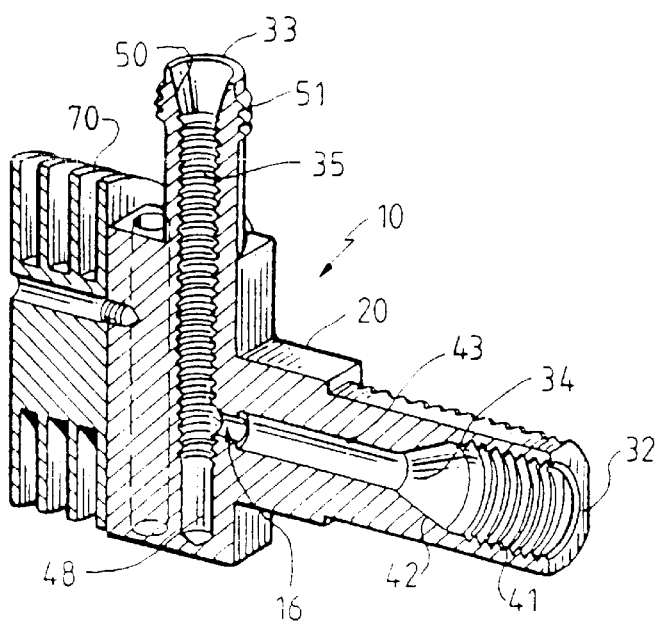
FIG. 6 is a perspective view, in section of the water management device of the present invention.

Also shown in FIG. 6 is a heat sink 70 attached to the water management device to direct heat away from the device. Not shown is an electric fan which is configured to blow air on the water management device for cooling of the device as will be described in more detail below. Although a fan is used in the preferred embodiment, a variety of conventional cooling apparatus may be used for this purpose.

The operation of the water management device during a typical sample concentration cycle will be described below. This process is microprocessor controlled with certain parameters that may be selected by the operator.

Figure 8:
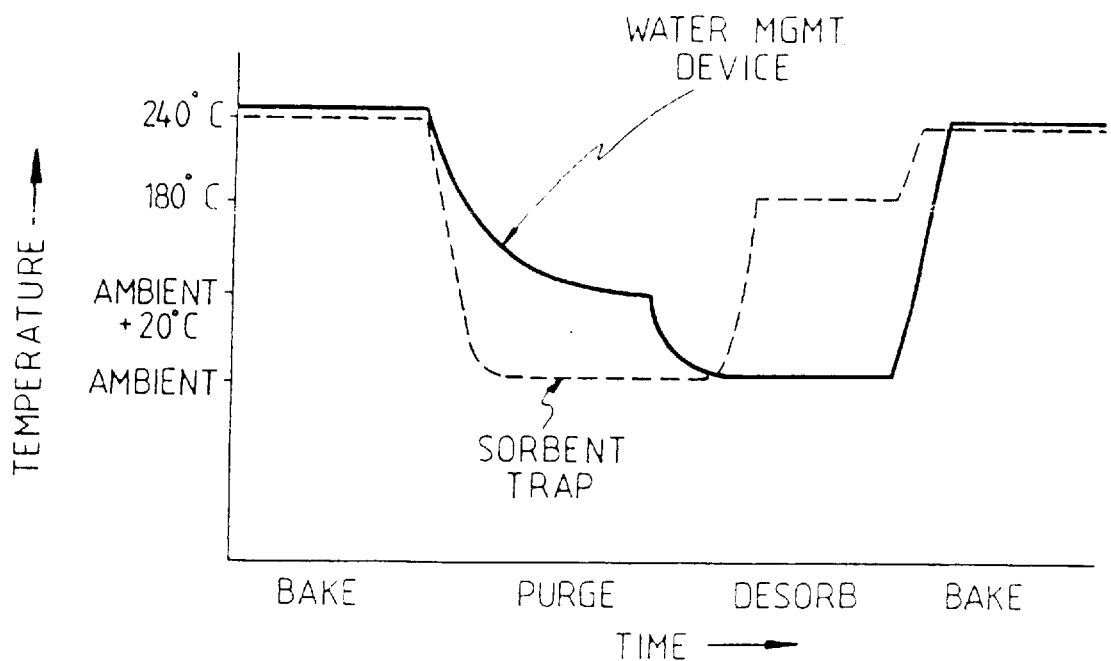
FIG. 8 is a plot of the temperature of the water management device of the present invention as a function of time.

As shown in FIG. 8, the sample concentration cycle includes the purge, desorb and bake steps. Typically, the purge step is 11 minutes, the desorb step is 4 minutes, and the bake step is at least 7 minutes. The vertical axis of FIG. 8 is the temperature of the water management device and sorbent trap in degrees C.

During the bake step, the water management device and trap are heated to an operator-selected temperature, preferably approximately 240 degrees C. In a preferred embodiment, the heating means for the water management device is the heating cartridge inserted in bore 61. The bake step serves to expel water vapor out of the system. During this step, bake gas may be introduced to flow through the trap and water management device, and out through vent 14.

Once the bake temperature has been reached, or following an operator-selected time period, the microprocessor activates a fan (not shown) to begin cooling the trap and the water management device. The mass of the water management device is larger than that of the trap, so it cools at a much slower rate.

Once the desired temperature is reached in the trap, preferably about 25 degrees C. or ambient temperature, as selected by the operator, the purge step begins. During this time, the water management device is cooled and/or heated to maintain its temperature at approximately 20 degrees higher than the temperature of the sample in the sparge vessel. Therefore, if the water sample is at 20 degrees C., the water management device is at 40 degrees C. To maintain the water management device at this temperature during the purge step, the heating cartridge and or fan are activated as needed by microprocessor control.

There is a significant advantage achieved with the water management device at a higher temperature than the trap during purge. During the purge step, it is intended that no condensation or other removal of water vapor from the analyte stream should occur. The higher temperature of the water management device prevents condensation from taking place before the analyte stream reaches the trap. If condensation occurred before reaching the trap, it is likely that condensed water vapor would remain in the water management device until the desorb step, when the water vapor and/or droplets would flow directly to the GC as the system is backflushed. Therefore, maintaining a higher temperature of the water management device during purge reduces the amount of water vapor that enters the GC, thereby improving detection of analytes.

As stated above, the purge step is typically about 4 minutes. Beginning in the last minute of purge, or at some other operator-selected time, the fan is activated to further cool the water management device. This is done to prepare the water management device for the desorb step which directly follows. During this final minute of purge, the water management device is cooled to (a) a selected temperature, or (b) a temperature at which the device stabilizes for a selected period of time, such as 20 seconds. The operator may select either of these parameters and temperatures. The temperature of the water management device tends to stabilize after approximately one minute, as further cooling of the water management device below ambient is extremely slow and difficult to achiever with only the fan as the cooling device. Therefore, if the selected temperature is not reached at the end of the selected time period, option (b) is the default parameter. At the end of purge, the desorb step does not begin until the selected temperature has been reached or the temperature of the water management device has stabilized for the selected time period.

When the water management device reaches the selected temperature, or maintains a stabilized temperature for the selected time period, the desorb step begins. In desorb, the trap is heated to a temperature of approximately 180 degrees C. by running electric current through the trap. The trap is back-flushed with carrier gas to remove the trapped analytes. The analyte slug then flows to the water management device on its way to the GC. While the trap is at 180 degrees C., the fan cools the water management device to ambient or another selected temperature which is generally slightly greater than ambient. Preferably, a short length of stainless steel tubing acts as a temperature buffer between the trap and the water management device. During desorb, the water management device removes water vapor from the analyte slug. At the end of the desorb step, the bake step repeats.

As shown in FIG. 9, under EPA Method 524.2 operating conditions the amount of water transfer to the GC with the present invention is substantially below that of the prior art. Without any water management system, the volume of water transfer to the GC is typically 11 mg. With the condensation approach of the OI Analytical Model 4460A, the volume of water transfer is approximately 1.1 mg. The present invention reduces the water transfer volume to only 0.25 mg.

One advantage of the present invention is that it allows a wider variety of sample temperature ranges. For example, the sample temperature can be from 0 to 100° C., whereas other means of water management did not work well above 30° C. Further, the water management device does not require cooling apparatus to bring its temperature below ambient room temperature. Since the water management device and sample are not cooled below ambient, the invention helps to reduce the "tailing" of the GC peaks caused by reduced temperature of prior art water management systems.

Another advantage of the present invention is that it reduces the "dead volume" that was present in prior art condensation devices used for water vapor removal. The reduction of "dead volume" enhances GC detection and analysis.

Another advantage to the present invention is that water vapor may be removed from the analyte slug without expensive and complex mechanical or electro-mechanical mechanisms that are subject to failure after repeated cycling.

Although variations in the embodiment of the present invention may not each realize all the advantages of the invention, certain features may become more important than others in various applications of the device. The invention, accordingly, should be understood to be limited only by the scope of the appended claims.

What is claimed is:

1. In a purge and trap system having a bake period, a purge period, and a desorb period, a method for removing water from a carrier gas flowing along a path in a water management device during the desorb period comprising:

purging the carrier gas along the water management device flow path, the flow path being at a purge temperature during the purge period such that condensation of water is substantially avoided;

cooling the water management device with a fan prior to or during the desorb period;

maintaining the flow path during the desorb period at a temperature lower than the purge temperature but not lower than ambient room temperature; and heating the water management device such that the flow path is at a bake temperature higher than the purge temperature during the bake period.

2. A method for removal of water from an analyte stream that is purged from a sparge vessel to a trap and desorbed from the trap to a gas chromatograph, comprising:

purging analytes from the sparge vessel and passing the purged analytes through a flow path connecting the sparge vessel to the trap, the flow path being at a purge temperature higher than the sparge vessel;

desorbing the analytes from the trap;

passing the desorbed analytes along the flow path from the trap to the gas chromatograph;

maintaining the flow path at a desorb temperature lower than the purge temperature but not lower than ambient room temperature;

heating the flow path to a bake temperature sufficient to expel water vapor from the flow path through a vent.

3. The method of claim 2, wherein the analyte stream flows in a helical path through the flow path.

4. The method of claim 2, wherein the flow path is helical.

5. The method of claim 2, wherein the analyte stream flows in a cylindrical path through the flow path.

6. The method of claim 2, wherein the flow path is cylindrical.

7. The method of claim 2, wherein the flow path is thermally isolated from the trap.

8. The method of claim 2, wherein a fan cools the flow path to the desorb temperature.

9. The method of claim 2, wherein the analyte stream flows along the flow path in opposite directions during purge and desorb.

10. The method of claim 2, wherein the purge temperature is sufficiently higher than the sparge vessel during purging to substantially prevent condensation of water in the flow path.

11. The method of claim 2, wherein a heating element heats the flow path.

12. The method of claim 2, wherein the flow path comprises a passage.

13. The method of claim 2, wherein the passage comprises two chambers at substantially right angles to each other.

* * * * *